United States Patent
Kim

(10) Patent No.: US 12,269,746 B2
(45) Date of Patent: Apr. 8, 2025

(54) ACTIVATED CARBON BALLS AND METHOD FOR PRODUCING THEREOF

(71) Applicants: AURA7 USA Inc, Henderson, NV (US); AURA7 CO., LTD, Henderson, NV (US)

(72) Inventor: Richard Jonghwan Kim, Henderson, NV (US)

(73) Assignee: AURA7 USA Inc, Henderson, NV (US)

( * ) Notice: Subject to any disclaimer, the term of this patent is extended or adjusted under 35 U.S.C. 154(b) by 788 days.

(21) Appl. No.: 17/073,154

(22) Filed: Oct. 16, 2020

(65) Prior Publication Data

US 2022/0024772 A1 Jan. 27, 2022

Related U.S. Application Data

(60) Provisional application No. 63/054,746, filed on Jul. 21, 2020.

(51) Int. Cl.
*C01B 32/324* (2017.01)
*A61F 7/00* (2006.01)
*A61N 5/06* (2006.01)

(52) U.S. Cl.
CPC .............. *C01B 32/324* (2017.08); *A61F 7/00* (2013.01); *A61N 5/06* (2013.01);
(Continued)

(58) Field of Classification Search
CPC ....... C01B 32/324; C01B 32/336; A61F 7/00; A61F 2007/0003; A61F 2007/0062;
(Continued)

(56) References Cited

U.S. PATENT DOCUMENTS 5,437,845 A * 8/1995 Brioni .................... C01B 32/39
422/198

OTHER PUBLICATIONS

Pomdee, et al., Characterization of carbon materials and differences from activated carbon particle (ACP) and coal briquettes product (CBP) derived from coconut shell via rotary kiln, Renewable and Sustainable Energy Reviews 2017; 75: 1175-1186 (Year: 2017).*

(Continued)

*Primary Examiner* — Daniel C. McCracken
(74) *Attorney, Agent, or Firm* — Barry Choobin; Patent 360

(57) ABSTRACT

The embodiments herein provide a method for producing activated carbonaceous balls. The method includes a step of crushing and sizing raw coconut shells to form coconut shell granules having a diameter of about 0.02 mm-2.36 mm, preferably 0.075 mm-1.18 mm. The method includes a step of mixing pure water to a food grade powder appropriately and boiling it slowly at 15° C.-80° C. to obtain a water-food grade powder mixture. The method includes a step of adding the water-food grade powder mixture 20-40% by weight to the coconut shell granules 100% by weight to obtain a slurry in a pourability condition. The method includes a step of pouring the slurry into a pill making machine equipped with a mold of 3 mm, 5 mm, and 8 mm in diameters selectively to produce the spherical carbon tablets. The method includes a step of drying the spherical carbon tablets and carbonizing the spherical carbon tablets to obtain the activated carbonaceous balls.

12 Claims, 6 Drawing Sheets

(52) U.S. Cl.
CPC ............... *A61F 2007/0003* (2013.01); *A61F 2007/0062* (2013.01); *A61N 2005/065* (2013.01); *A61N 2005/066* (2013.01)

(58) Field of Classification Search
CPC ...... A61F 2007/0059; A61F 2007/0088; A61F 2007/0098; A61N 5/06; A61N 2005/065; A61N 2005/066
See application file for complete search history.

(56) References Cited

OTHER PUBLICATIONS

Hu, et al., Preparation of high-surface-area activated carbons from coconut shell, Microporous and Mesoporous Materials 1999; 27: 11-18 (Year: 1999).*

\* cited by examiner

ACTIVATED CARBON BALLS AND METHOD FOR PRODUCING THEREOF

CROSS-REFERENCE TO RELATED APPLICATIONS

The embodiments herein claim the priority of the US Provisional Patent Application (PPA) filed on Jul. 21, 2020, with the Ser. No. 63/054,746 with the title, "Manufacturing of activated carbon balls by using coconut shells in a range of 3 mm to 8 mm in diameter and its use for dietary supplement", and the contents of which are included in entirety as reference herein.

BACKGROUND

Technical Field

The embodiments herein are generally related to the field of activated carbon balls. The embodiments herein are particularly related to activated carbon balls for dietary supplement use. The embodiments herein are more particularly related to activated carbon balls and method for producing thereof.

Description of the Related Art

Generally, activated carbons are used in various industries such as the food industry, chemical industry, and medicine industry, etc. Activated carbons have been studied and researched for decades by scientists and researchers at large for various industrial applications. The dust or ash-like activated carbons are available for use in the market as a dietary supplement for food poisoning relief, intestinal gas detoxification, etc.

U.S. Pat. No. 4,822,765A filed by Nishimura discloses an antidote that consists of spherical particles of activated carbon including at least 85% in the number of microscopically spherical particles of activated carbon and is useful in removing poisonous or harmful substances from the gastrointestinal tracts. The side effect of repeated intake of the small particle size of 0.05 to 2 mm in diameter causes constipation. In this context, the demand for highly antidotally effective activated carbon development of particle size larger than 2 mm in diameter is strongly desired.

Canadian patent CA2150184A1 filed by Uehara Yasuo et al. discloses a method of treating a patient suffering from inflammatory bowel diseases, comprising orally administering to said patient an effective amount of a pharmaceutical composition in dosage unit form comprising a spherical activated carbon having a particle size of 0.05 to 2 mm.

This specification recognizes there is a need for an efficient method to produce activated carbon balls larger than 2 mm in diameter for which can be used as a dietary supplement for chronic constipation and bowel health.

The above-mentioned shortcomings, disadvantages, and problems are addressed herein and which will be understood by reading and studying the following specification.

SUMMARY

The various embodiments herein provide a method for producing activated carbon balls for dietary supplement use. According to an embodiment herein, a method for producing a plurality of activated carbonaceous balls is provided.

According to an embodiment herein, the method includes a step of crushing and sizing raw coconut shells to form coconut shell granules having a diameter of about 0.02 mm-2.36 mm, preferably 0.075 mm-1.18 mm. The method includes a step of mixing pure water to a food grade powder appropriately and boiling it slowly at 15° C.-80° C. to obtain a water-food grade powder mixture. The method includes a step of adding the water-food grade powder mixture 20-40% by weight to the coconut shell granules 100% by weight to obtain a slurry in a pourability condition. The method includes a step of pouring the slurry into a pill making machine equipped with a mold of 3 mm, 5 mm, and 8 mm in diameters selectively to produce a plurality of spherical carbon tablets. The method includes a step of drying the plurality of spherical carbon tablets. The method includes a step of carbonizing the plurality of spherical carbon tablets to obtain the plurality of activated carbonaceous balls.

In an aspect, the raw coconut shells comprising a cellular membrane containing a binding agent. In addition, lignin acts as the binding agent.

In an aspect, the spherical carbon tablets are dried by utilizing a mechanical oven at a temperature of about 20° C.-80° C. for 1 hour-4 hours.

In an aspect, the spherical carbon tablets are dried by utilizing natural air drying at the ambient temperature for 2-3 days.

In an aspect, the spherical carbon tablets are carbonized in an air-tight kiln with a steam exit at a temperature of 450° C.-1000° C. for 1-5 days.

In an aspect, the activated carbonaceous balls are produced for use with a portable facial hot steamer.

In an aspect, the portable facial hot steamer performs hot steaming on the activated carbonaceous balls to generate far infrared (FIR) rays.

According to an embodiment herein, the plurality of activated carbonaceous balls are produced by a process including crushing and sizing raw coconut shells to form coconut shell granules having a diameter of about 0.02 mm-2.36 mm, preferably 0.075 mm-1.18 mm; mixing pure water to a food grade powder appropriately and boiling it slowly at 15° C.-80° C. to obtain a water-food grade powder mixture; adding the water-food grade powder mixture 20-40% by weight to the coconut shell granules 100% by weight to obtain a slurry in a pourability condition; pouring the slurry into a pill making machine equipped with a mold of 3 mm, 5 mm, 8 mm in diameters selectively to produce a plurality of spherical carbon tablets; drying the plurality of spherical carbon tablets; and carbonizing the plurality of spherical carbon tablets to produce the plurality of activated carbonaceous balls.

In an aspect, the raw coconut shells comprising a cellular membrane containing a binding agent.

In an aspect, the spherical carbon tablets are dried by utilizing a mechanical oven at a temperature of about 20° C.-80° C. for 1 hour-4 hours.

In an aspect, the spherical carbon tablets are dried by utilizing natural air drying at the ambient temperature for 2-3 days.

In an aspect, the spherical carbon tablets are carbonized in an air-tight kiln with a steam exit at a temperature of 450° C.-1000° C. for 1-5 days.

In an aspect, the plurality of activated carbonaceous balls are produced for use with a portable facial hot steamer.

In an aspect, the portable facial hot steamer performs hot steaming on the plurality of activated carbonaceous balls to generate far infrared (FIR) rays.

These and other aspects of the embodiments herein will be better appreciated and understood when considered in conjunction with the following description and the accompanying drawings. It should be understood, however, that the following descriptions, while indicating the preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features, and advantages will occur to those skilled in the art from the following description of the preferred embodiment and the accompanying drawings in which.

Figure 1:
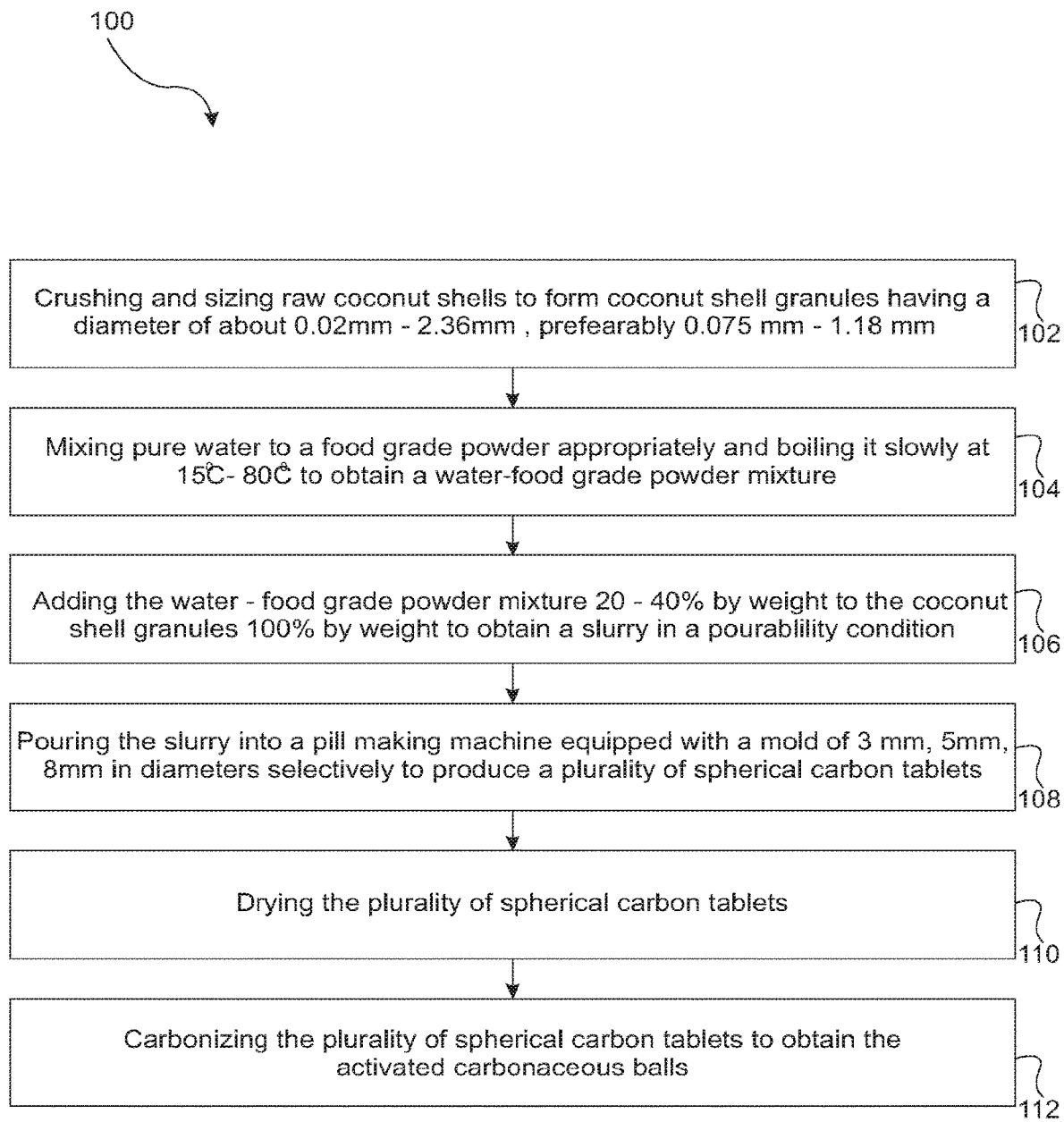
FIG. 1 illustrates a flowchart of a method for producing a plurality of activated carbonaceous balls, in accordance with an embodiment.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS HEREIN

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical, and other changes may be made without departing from the scope of the embodiments. The following detailed description is therefore not to be taken in a limiting sense.

The various embodiments herein provide a method for the manufacturing of activated carbonaceous balls by using coconut shells to produce highly carbonized tablets for human consumption as a dietary supplement. The activated carbonaceous balls are manufactured through the process have excellent absorption function. In an embodiment, the activated carbonaceous balls may refer to activated carbon tablets or activated carbonaceous composition or spherical activated carbon products, or activated charcoal balls. The activated carbonaceous balls can be taken orally to detoxify the bowels for the solution of chronic constipation. The characteristics of activated carbons are to absorb toxic materials if taken orally and discharge them out of the body. In an embodiment, the activated carbonaceous balls are produced by using coconut shells sourced from tropical climate regions and the coconut shells contain high-quality lignin that exists in the cellular membrane of coconut shells.

The lignin is termed in other words as a natural plant-based binding polymer. Pure water and the food-grade powder are mixed with crushed coconut shell granules to come to a slurry mixture to pour into the pill making machine equipped with mold in size 3 mm, 5 mm, 8 mm in diameter selectively to produce spherical activated charcoal balls. Those activated charcoal balls are dried in a mechanical oven or for air drying for 24 hours and then put into the heated kiln with a steam exit for carbonization. The activated charcoal balls (spherical or oblong) are also to be beneficially utilized in conjunction with a hot facial steamer for commercial use for human health and beauty benefits.

According to one embodiment herein, a method for producing a plurality of activated carbonaceous balls are provided. The description highlights several embodiments of the invention provided mainly as examples to better describe the disclosure without limiting the scope of the invention. These embodiments describe different configurations, arrangements, features, and methods along with various figures to schematically describe them. The embodiments are frequently referred to each other, which by itself do not constitute a relationship between them. Moreover, it is possible to combine the features or parts of one embodiment with that of another embodiment in different ways without deviating from the scope of this disclosure.

Also, certain terminologies and naming conventions have been used throughout this description. As one skilled in the art may appreciate, it is possible to use different names to refer to the same idea or feature, which will not limit the scope of the invention, unless specifically mentioned otherwise. The functionality of the various parts of the embodiments should be assigned importance over the names by which they are referred to, as the names by themselves are meant only for differentiation. Numerical values stated in this disclosure may be approximate or exact unless otherwise mentioned specifically and the various embodiments may deviate from the stated numbers without deviating from the intended scope.

FIG. 1 illustrates a flowchart 100 of a method for producing a plurality of activated carbonaceous balls, in accordance with an embodiment. The method includes a step 102 of crushing and sizing raw coconut shells to form coconut shell granules having a diameter of about 0.02 mm-2.36 mm, preferably 0.075 mm-1.18 mm. In an embodiment, the raw coconut shells comprising a cellular membrane containing a binding agent. In addition, lignin acts as the binding agent. In an embodiment, the raw coconut shells contain highly concentrated lignin that naturally exists in the cell membrane of the coconut shells. The lignin acts as a very strong natural binder in the process of heating and carbonization. The method includes a step 104 of mixing pure water to a food grade powder appropriately and boiling it slowly at 15° C.-80° C. to obtain a water-food grade powder mixture. In an embodiment, the food grade powder is strong flour. Typically, strong flour is made by grinding hard wheat grains in a process known as milling. Hard wheat grains refer to kernels that have a high protein content. The method includes a step 106 of adding the water-food grade powder mixture 20-40% by weight to the coconut shell granules 100% by weight to obtain a slurry in a pourability condition. The method includes a step 108 of pouring the slurry into a pill making machine equipped with a mold of 3 mm, 5 mm, and 8 mm in diameters selectively to produce a plurality of spherical carbon tablets. The method includes a step 110 of drying the plurality of spherical carbon tablets. In an embodiment, the spherical carbon tablets are dried by utilizing a mechanical oven at a temperature of about 20°

C.-80° C. for 1 hour-4 hours. In an embodiment, the spherical carbon tablets are either dried by utilizing natural air drying at the ambient temperature for 2-3 days. The method includes a step 112 of carbonizing the plurality of spherical carbon tablets to obtain the plurality of activated carbonaceous balls. In an embodiment, the spherical carbon tablets are carbonized in an air-tight kiln with a steam exit at a temperature of 450° C.-1000° C. for 1-5 days.

According to an embodiment herein, strong flour is used to be able to mix coconut shell granules to be able to shape it. The pure water and strong flour are evaporated during the process of high-temperature carbonization. During the carbonization process, lignin reacts to bond coconut shell granules to provide its strength and stability. Further, during the carbonization process, a huge cross-linked surface area and space or pore volume between layers of the surface are created that can absorb a huge amount of toxic materials. The activated carbonaceous balls absorb only unwanted toxic materials and get them out of a user's body. In an embodiment, the activated charcoal balls can often be used for food poisoning relief.

Figure 2:
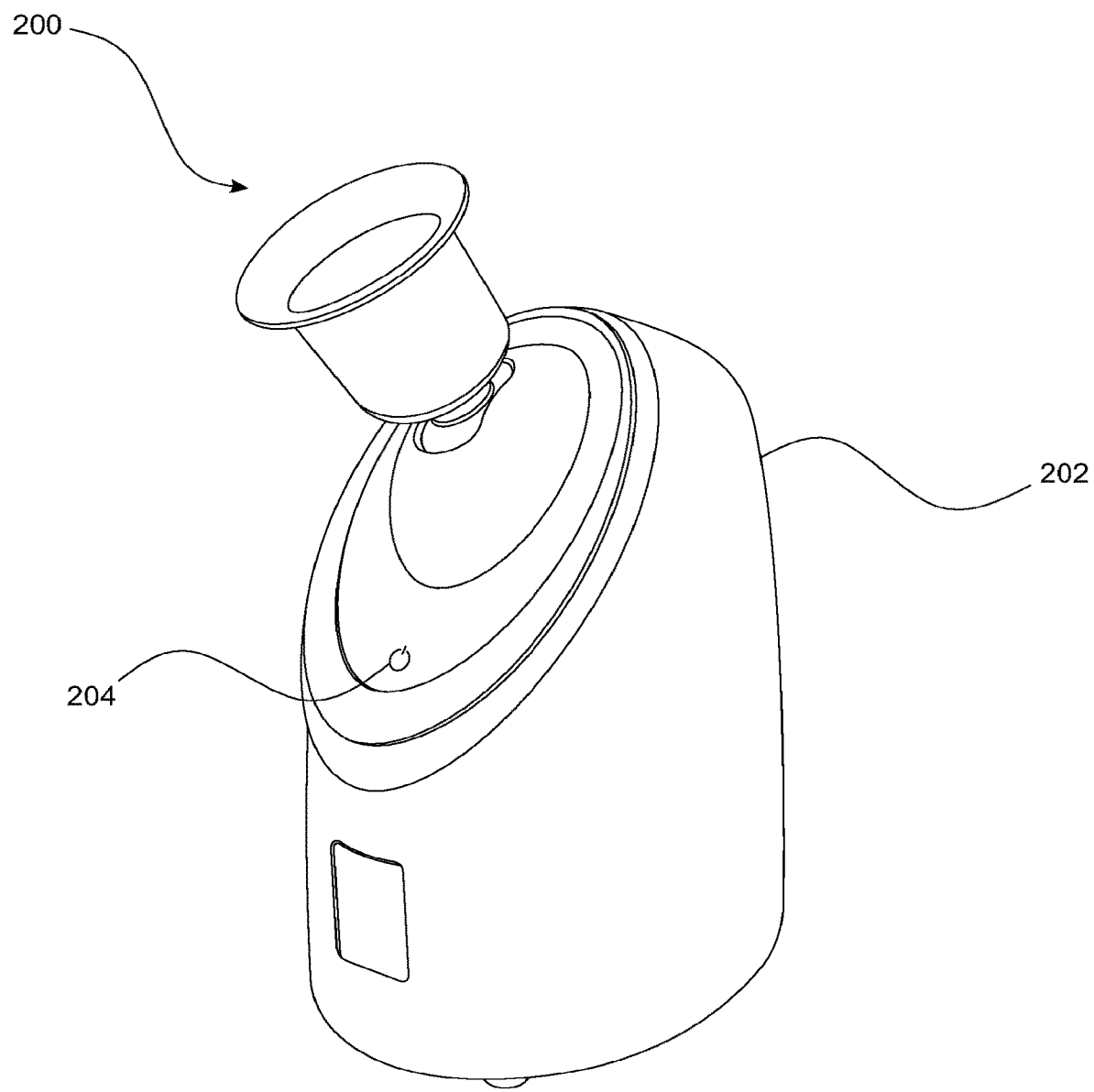
FIG. 2 illustrates a perspective view of a portable facial hot steamer, according to one embodiment herein.
Figure 3:
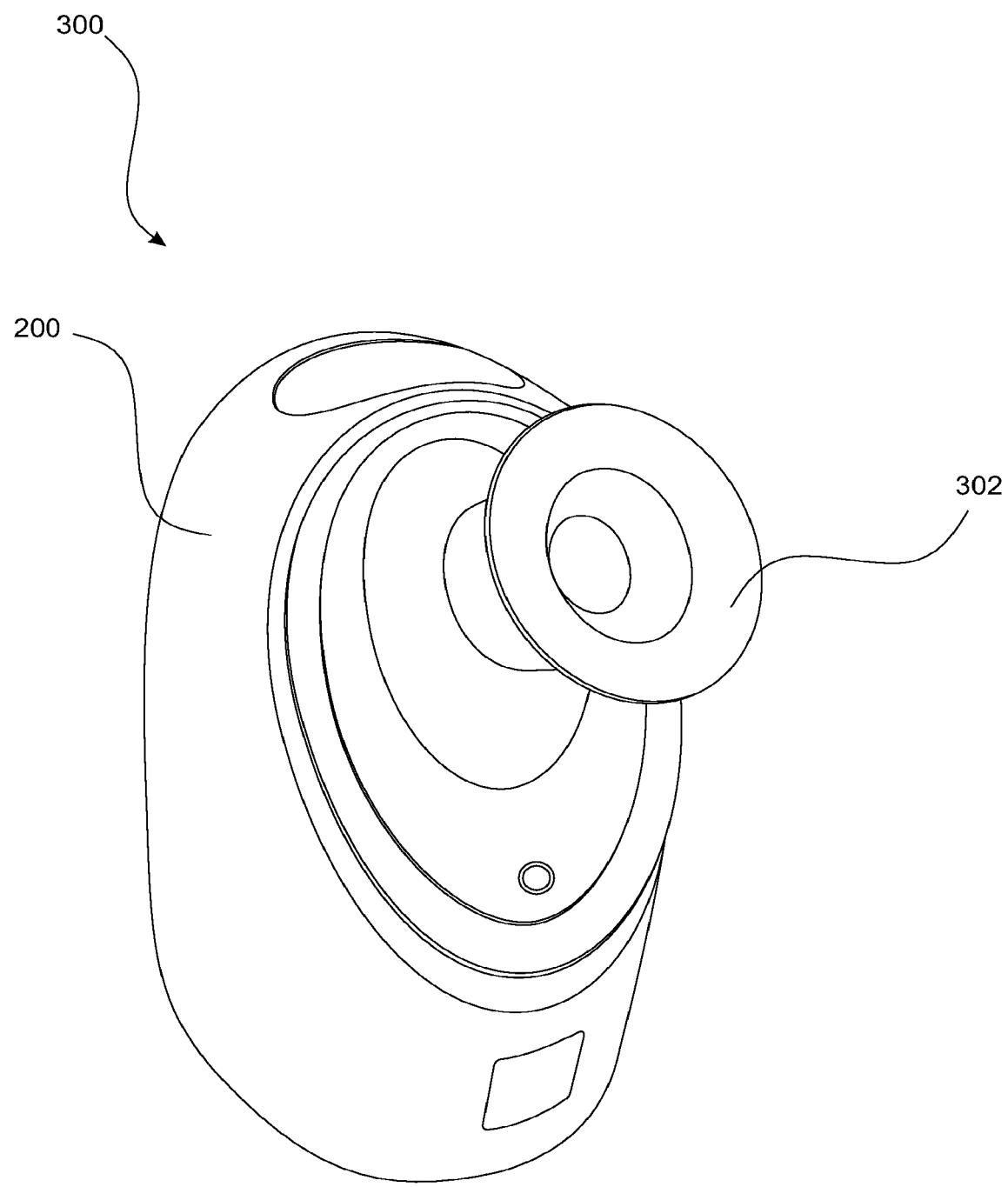
FIG. 3 illustrates an operational view of a portable facial hot steamer, according to one embodiment herein.

FIG. 2 illustrates a perspective view of a portable facial hot steamer 200, that has been developed in conjunction with the use of activated carbonaceous balls for hot steaming purposes. The portable facial hot steamer 200 having a casing 202 which contains a removable and fillable water tank with a capacity of 220 ml to be heated into steam. The portable facial hot steamer 200 includes a power button 204 to receive a press gesture from the user to start the operation, electrically heat the water to generate the steam, and automatically turns off when the water is depleted in the water tank. FIG. 3 illustrates an operational view 300 of a portable facial hot steamer, according to one embodiment herein. The portable facial hot steamer 200 performs hot steaming 302 on the activated carbonaceous balls deposited in the stainless steel basket with a locking lid installed inside the nozzle to generate far infrared (FIR) rays. Typically, far infrared rays are radiation with a wavelength of 15 micrometers to 1 mm. The wavelength is too long to be perceived by the eyes; however, the body experiences its energy as a gentle radiant heat that can penetrate up to 1.5 inches beneath the skin.

Figure 4:
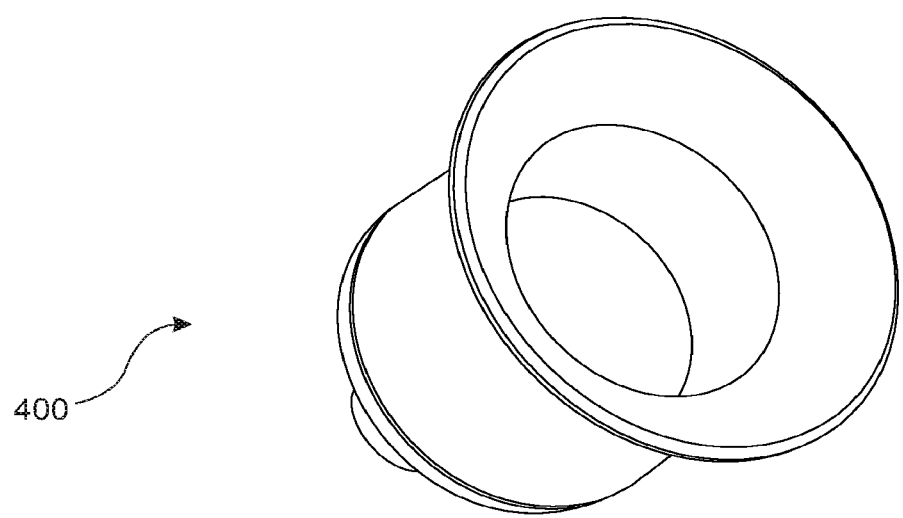
FIG. 4 illustrates a perspective view of a nozzle of the portable facial hot steamer, according to one embodiment herein.
Figure 5:
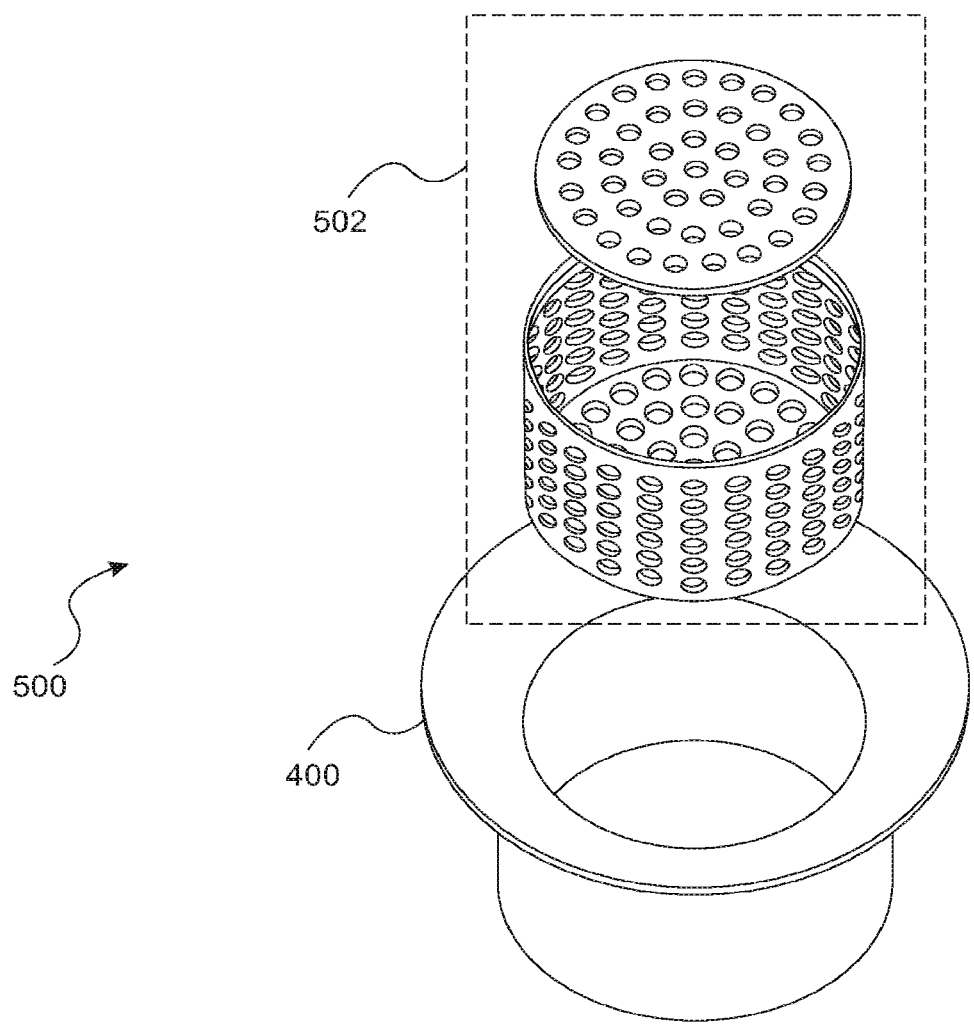
FIG. 5 illustrates an exploded view of the nozzle and a basket with a lid of the portable facial hot steamer, according to one embodiment herein.

FIG. 4 illustrates a perspective view of a nozzle 400 of the portable facial hot steamer, according to one embodiment herein. The portable facial hot steamer 200 includes a nozzle 400 to discharge and control the direction of the steam. FIG. 5 illustrates an exploded view 500 of the nozzle of the portable facial hot steamer, according to one embodiment herein. FIG. 5 is explained in conjunction with FIG. 4. The nozzle 400 can be detachably attached to the casing 202 of the portable facial hot steamer 200 by clicking in and the nozzle 400 can be moved up or down to adjust the height. In an embodiment, the basket with lid 502 is made of stainless steel and the nozzle is made of Acrylonitrile Butadiene Styrene (ABS) plastic. In an embodiment, the nozzle 400 houses the basket with lid 502 which is designed to contain activated charcoal balls in quantity for hot steaming purpose. The nozzle 400 is removably attached to the top end of the casing of the portable facial hot steamer 200.

Figure 6:
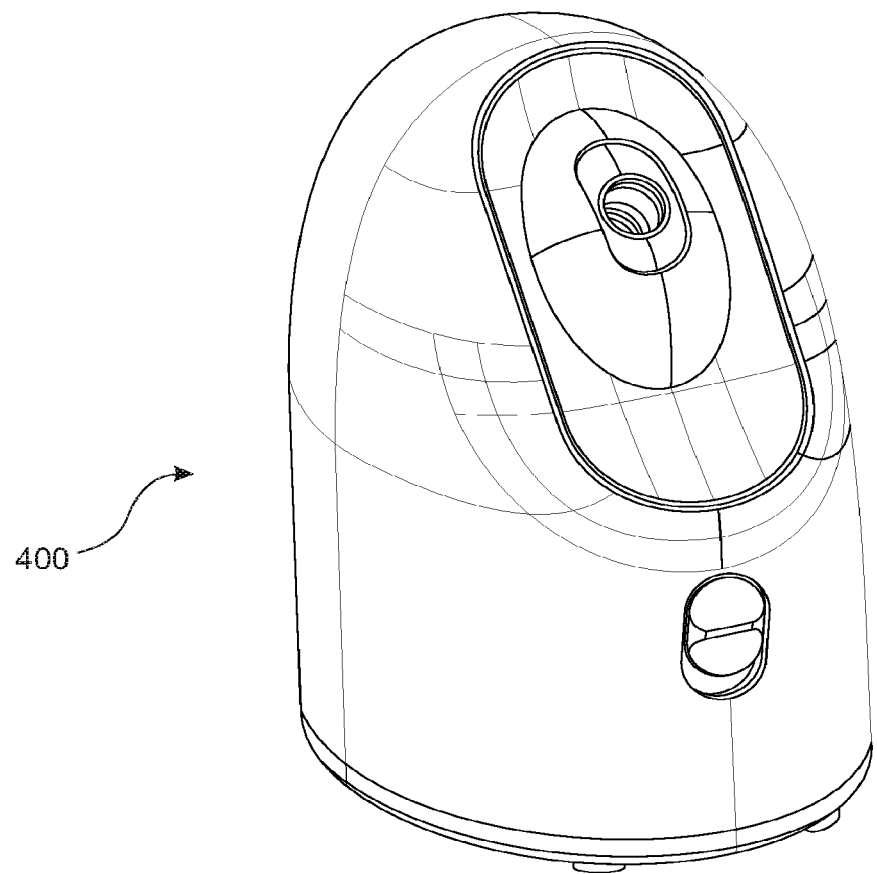
FIG. 6 illustrates a perspective view of the portable facial hot steamer without nozzle before attachment of the nozzle to the facial steamer, according to one embodiment herein.

FIG. 6 illustrates a perspective view 600 of the portable facial hot steamer without nozzle, according to one embodiment herein. The customers can attach or detach the nozzle to the portable facial hot steamer as needed just simply by clicking-in or clicking-out conveniently.

According to an embodiment herein, the plurality of activated carbonaceous balls are produced by a process including crushing and sizing raw coconut shells to form coconut shell granules having a diameter of about 0.02 mm-2.36 mm, preferably 0.075 mm-1.18 mm; mixing pure water to a food grade powder appropriately and boiling it slowly at 15° C.-80° C. to obtain a water-food grade powder mixture; adding the water-food grade powder mixture 20-40% by weight to the coconut shell granules 100% by weight to obtain a slurry in a pourability condition; pouring the slurry into a pill making machine equipped with a mold of 3 mm, 5 mm, 8 mm in diameters selectively to produce a plurality of spherical carbon tablets; drying the plurality of spherical carbon tablets; and carbonizing the plurality of spherical carbon tablets to produce the plurality of activated carbonaceous balls.

In an embodiment, the raw coconut shells comprising a cellular membrane containing a binding agent. In addition, lignin acts as the binding agent. In an embodiment, the spherical carbon tablets are dried by utilizing a mechanical oven at a temperature of about 20° C.-80° C. for 1 hour-4 hours. In an embodiment, the spherical carbon tablets are either dried by utilizing natural air drying at the ambient temperature for 2-3 days. In an embodiment, the spherical carbon tablets are carbonized in an air-tight kiln with a steam exit at a temperature of 450° C.-1000° C. for 1-5 days. In an embodiment, the activated carbonaceous balls are produced for use with a portable facial hot steamer. The main characteristics of activated carbonaceous balls are the absorption function of unwanted waste and toxic materials through the pores volume and surface areas created through the carbonization process.

In an embodiment, the portable facial hot steamer performs hot steaming on the activated carbonaceous balls to generate far infrared (FIR) rays. Additionally, hot steaming of the activated carbonaceous balls radiates far infrared rays beneficial for various human uses. Among the various benefits of the uses are prevention of viruses (humidity and hot temperature 40-45 degrees Celsius not viable condition for viruses), acne, ozena, various inflammations, and pain relief and dry eye symptoms. Far infrared rays are radiated when steaming activated carbonaceous balls and some of the major beneficial effects on the human body of the far infrared rays are observed. The steam radiated through the portable facial hot steamer 200 provides various advantages such as to help maintain the body temperature at an appropriate level and make inner temperature warmer than the outer body temperature, accelerate the body growth, release the pain of heat and burn scars, actively contribute to the scar healing process, purify the blood for excellent blood circulation, maintain the appropriate level of humidity, and neutralize the smell by attaching and discharging the impurities. The active perspiration by hot steaming of activated carbonaceous balls can contribute to discharging of the accumulated impurities, toxic metals, pesticides, harmful pigments, and residue fats out of the body. Especially it can reduce the excess salt accumulated in the body through a long period of eating habits. Additionally, the impurities and residual cosmetics accumulated in the skin and blocking the skin metabolism can be discharged by perspiration caused by hot steaming. The excess fat in the fat gland can be discharged resulting in ever shiny and brightening skin conditions.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

The embodiments herein provide a method for producing a plurality of activated carbonaceous balls. This technology helps to provide a dietary supplement for chronic constipation and bowel health and weight management. Another advantage of the embodiments herein the activated carbonaceous balls are produced for use in conjunction with a portable facial hot steamer.

The foregoing description of the specific embodiments will so fully reveal the general nature of the embodiments herein that others can, by applying current knowledge, readily modify and/or adapt for various applications such as specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modifications. However, all such modifications are deemed to be within the scope of the claims.

What is claimed is:

1. A method for producing activated carbonaceous balls, the method comprising:
   crushing and sizing raw coconut shells to form coconut shell granules having a diameter in a range of about 0.02 mm-2.36 mm;
   mixing water to a food grade powder and boiling it at 15° C.-80° C. to obtain a water-food grade powder mixture;
   adding the water-food grade powder mixture 20-40% by weight to the coconut shell granules 100% by weight to obtain a slurry in a pourability condition;
   pouring the slurry into a pill-making machine equipped with a mold of 3 mm, 5 mm, and 8 mm diameters to produce spherical carbon tablets;
   drying the spherical carbon tablets; and
   carbonizing the spherical carbon tablets to obtain the activated carbonaceous balls.

2. The method as claimed in claim 1, wherein the raw coconut shells comprise a cellular membrane containing a binding agent.

3. The method as claimed in claim 1, wherein the spherical carbon tablets are dried in a mechanical oven at a temperature of about 20° C.-80° C. for 1-4 hours.

4. The method as claimed in claim 1, wherein the spherical carbon tablets are dried using natural air at ambient temperature for 2-3 days.

5. The method as claimed in claim 1, wherein the spherical carbon tablets are carbonized in an air-tight kiln with a steam exit at a temperature of 450° C.-1000° C. for 1-5 days.

6. The method as claimed in claim 1, wherein the method further comprises:
   using the activated carbonaceous balls with a portable facial hot steamer.

7. The method as claimed in claim 6, wherein the portable facial hot steamer performs hot steaming on the activated carbonaceous balls to generate far infrared (FIR) rays.

8. Activated carbonaceous balls produced by a process comprising:
   crushing and sizing raw coconut shells to form coconut shell granules having a diameter in a range of about 0.02 mm-2.36 mm;
   mixing water to a food grade powder and boiling it at 15° C.-80° C. to obtain a water-food grade powder mixture;
   adding the water-food grade powder mixture 20-40% by weight to the coconut shell granules 100% by weight to obtain a slurry in a pourability condition;
   pouring the slurry into a pill making machine equipped with a mold of 3 mm, 5 mm, and 8 mm diameters to produce spherical carbon tablets;
   drying the spherical carbon tablets; and
   carbonizing the spherical carbon tablets to produce the activated carbonaceous balls.

9. The activated carbonaceous balls as claimed in claim 8, wherein the raw coconut shells comprise a cellular membrane containing a binding agent.

10. The activated carbonaceous balls as claimed in claim 8, wherein the spherical carbon tablets are dried in a mechanical oven at a temperature of about 20° C.-80° C. for 1 hour-4 hour.

11. The activated carbonaceous balls as claimed in claim 8, wherein the spherical carbon tablets are dried using natural air at an ambient temperature for 2-3 days.

12. The activated carbonaceous balls as claimed in claim 8, wherein the spherical carbon tablets are carbonized in an air-tight kiln with a steam exit at a temperature of 450° C.-1000° C. for 1-5 days.

* * * * *